United States Patent
Shimamura et al.

(10) Patent No.: US 6,476,364 B1
(45) Date of Patent: Nov. 5, 2002

(54) APPARATUS FOR CONTROLLING A TIMING OF TURNING ON ELECTRICITY TO A HEATER

(75) Inventors: Koichi Shimamura; Koji Kano; Mitsuo Kusa, all of Saitama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/404,248

(22) Filed: Sep. 22, 1999

(30) Foreign Application Priority Data

Sep. 22, 1998 (JP) .......................... 10-268618

(51) Int. Cl.$^7$ ............................... H05B 1/02
(52) U.S. Cl. .................. 219/494; 219/497; 123/697; 73/23.32
(58) Field of Search ................ 219/494, 497, 219/499, 501, 507, 505; 73/23.31, 23.32, 1.63; 123/684, 676, 697

(56) References Cited

U.S. PATENT DOCUMENTS 5,405,521 A * 4/1995 Nakamori et al. .......... 204/425
5,901,553 A * 5/1999 Cullen .......................... 60/274
6,314,790 B1 * 11/2001 Sagisaka et al. ........... 73/23.31

FOREIGN PATENT DOCUMENTS

| JP | A59-214756 | 12/1984 |
| JP | U5-84852 | 11/1993 |
| JP | B2 7-99365 | 10/1995 |

* cited by examiner

Primary Examiner—Mark Paschall
(74) Attorney, Agent, or Firm—Birch, Stewart, Kolasch & Birch, LLP (57) ABSTRACT

An apparatus for controlling operation of a heater has an internal resistance detector for detecting an internal resistance value of an oxygen sensor, and a control unit for estimating a surface temperature of the oxygen sensor based on the internal resistance value detected by the internal resistance detector, then estimating a temperature of the exhaust pipe based on the estimated surface temperature of the oxygen sensor and controlling the operation of the heater, which is combined with the oxygen sensor in a single unit, when the estimated temperature of the exhaust pipe has reached a predetermined temperature.

12 Claims, 5 Drawing Sheets

APPARATUS FOR CONTROLLING A TIMING OF TURNING ON ELECTRICITY TO A HEATER

BACKGROUND OF THE INVENTION

1. Field of the Invention

This invention relates to an apparatus for controlling the temperature of an oxygen sensor, which is mounted on an exhaust pipe to control an air/fuel ratio of an internal combustion engine, and more particularly to an apparatus for controlling activation of a heater of the oxygen sensor by turning off the electricity to the heater when the temperature of the exhaust pipe, when the engine is started is low, or when condensation left in the exhaust pipe or is likely to occur in the exhaust pipe.

2. Description of Background Art

A conventional oxygen sensor has varying conductivity and electromotive force if there is a difference in oxygen concentration between confronting surfaces of two electrodes of the oxygen sensor, which are arranged with a solid electrolyte interposed therebetween.

Using the oxygen sensor, a difference in concentration between oxygen contained in exhaust gas in an exhaust pipe and the oxygen in the atmosphere is detected in terms of internal resistance variation in conductivity and/or electromotive force. The variation of the detected value is then provided to a control unit to control a fuel injection time period in such a manner that the intake mixed gas achieves a theoretical air/fuel ratio.

The term "theoretical air/fuel ratio" is a ratio of air and fuel by weight for a theoretically required minimum amount of air, under the hypothesis that mixed gas introduced into a combustion chamber can be burned perfectly.

In a gasoline engine, the typical theoretical air/fuel ratio has an air component which is in the order of 14.5–15, and a fuel component which is in the order of 1.

Controllers are known which detect a temperature of the exhaust pipe at a time of starting an internal combustion engine. These controllers use a temperature sensor in the exhaust pipe, then detect an element temperature of an oxygen sensor by an element temperature detector, and control a heater of the oxygen sensor in such a manner that the oxygen sensor temperature does not exceed a predetermined temperature until the exhaust pipe temperature detected by the temperature sensor has exceeded 100° C. (For example, see Japanese Utility Model Laid-Open Publication No. Hei 5-84852).

Furthermore, controllers have been proposed in which an internal resistance of an oxygen sensor is estimated. This approach is used because, as is commonly known, an oxygen sensor operates stably when a high temperature, an internal resistance value and an oxygen sensor temperature correlate. The heater is controlled in such a manner that the oxygen temperature is kept normally constant within a high temperature range exceeding a predetermined temperature. (For example, see Japanese Patent Publication No. Hei 7-99365 and Japanese Patent Laid-Open Publication No. Sho 59-214756).

However, the conventional electricity controllers require a temperature sensor for detecting that an exhaust pipe temperature is sufficiently high enough to eliminate condensation. The temperature effectively prevents thermal shock to the oxygen sensor thereof immediately after the internal combustion engine has been started; however, such a design has increased the cost of production.

Another problem with the conventional controllers is that the method of either assembling or mounting the temperature sensor is complex, thereby ensuring large production cost requirements and requiring significant cost when maintenance is required.

As indicated with the conventional controllers for estimating an internal resistance of the oxygen sensor, it is possible to keep the temperature of the oxygen sensor normally constant at an optimum temperature by way of a heater. This keeps the internal resistance value of the oxygen sensor constant. However, these conventional controllers encounter still another problem. Although a temperature of the oxygen sensor can be determined from an internal resistance thereof, it can not estimate, for an exhaust pipe in question, a temperature when condensation will develop in the exhaust pipe.

SUMMARY OF THE INVENTION

With the foregoing problems in view, it is therefore an object of this invention to provide an inexpensive apparatus for controlling the timing of turning on and off the electricity to an oxygen sensor heater in order to prevent thermal shock, without using an exhaust pipe temperature sensor, even when condensation develops in the exhaust pipe because the temperature of the exhaust pipe, which communicates with the internal combustion engine, is low.

In order to attain the above-mentioned object, according the present invention, there is provided an apparatus for controlling the timing of turning on the electricity to a heater by controlling the temperature of an oxygen sensor, which is mounted on an exhaust pipe to control an air/fuel ratio of an internal combustion engine, comprising: internal resistance detecting means for detecting an internal resistance value of the oxygen sensor; and controlling means for estimating a surface temperature of the oxygen sensor based on the internal resistance value detected by the internal resistance detecting means, then estimating a temperature of the exhaust pipe based on the estimated surface temperature of the oxygen sensor and controlling the starting of turning on the electricity to the heater, which is combined with the oxygen sensor in a single unit, when the estimated temperature of the exhaust pipe has reached a predetermined temperature.

With this arrangement, since there are provided internal resistance detecting means for detecting an internal resistance value of the oxygen sensor and controlling means for estimating a surface temperature of the oxygen sensor based on the internal resistance value detected by the internal resistance detecting means, then estimating a temperature of the exhaust pipe based on the estimated surface temperature of the oxygen sensor and starting turning on the electricity to a heater, which is combined with the oxygen sensor into a single unit, when the estimated exhaust pipe temperature has reached a predetermined temperature, it is possible to prevent turning on the electricity to the heater while condensation remains in the exhaust pipe because the exhaust pipe temperature is low and until after such condensation has disappeared. Thus, it is possible to control the timing of turning on the electricity to the heater with a simple structure.

As a preferred feature, the heater control apparatus further comprises an intake temperature sensor for detecting an intake temperature. Thus, the controlling means controls the timing of turning on the electricity to the heater based on the estimated exhaust pipe temperature and the detected intake temperature.

With this preferred arrangement, partly since the intake temperature sensor is provided for detecting an intake temperature and partly since the controlling means controls the starting of turning on the electricity to the heater based on the estimated exhaust pipe temperature and the detected intake temperature, it is possible to heat the oxygen sensor when no condensation remains in the exhaust pipe.

As another preferred feature, the heater control apparatus further comprises an engine water temperature sensor for detecting an engine water temperature. Thus, the controlling means controls the timing of turning on the electricity to the heater based on the estimated exhaust pipe temperature and the detected engine water temperature.

With another preferred arrangement, partly since the engine water temperature sensor is provided for detecting an engine water temperature, and partly since the controlling means controls turning on the electricity to the heater based on the estimated exhaust pipe temperature and the detected engine water temperature, it is possible to heat the oxygen sensor when no condensation is in the exhaust pipe.

As still another preferred feature, the heater control apparatus further comprises an intake temperature sensor and an engine water temperature sensor. The controlling means detects an intake temperature and an engine water temperature and controls the timing of turning on the electricity to the heater based on the estimated exhaust pipe temperature, the detected intake temperature and the detected engine water temperature.

With still another preferred arrangement, partly since the intake temperature sensor and the engine water temperature sensor are provided, and partly since the controlling means controls the timing of turning on the electricity to the heater based on the estimated exhaust pipe temperature, the detected intake temperature and the detected engine water temperature, it is possible to heat the oxygen sensor when no condensation remains in the exhaust pipe.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
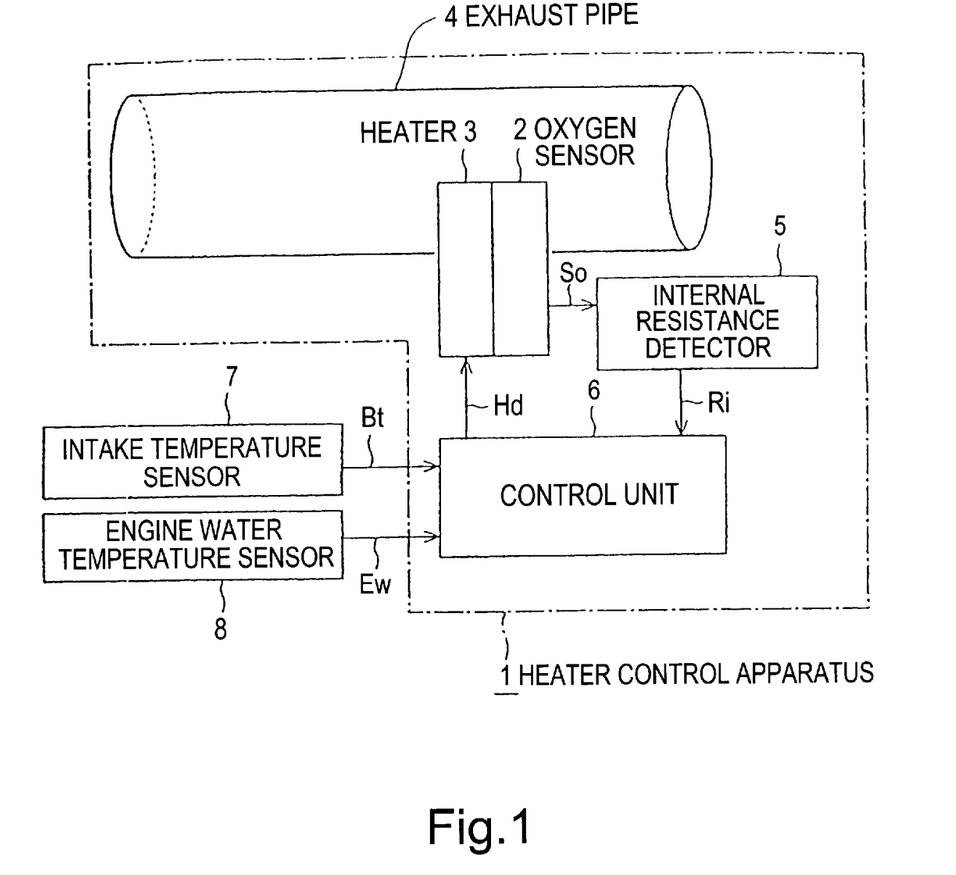
FIG. 1 is a block diagram showing a principal part of a heater control apparatus according to this invention.

As illustrated in FIG. 1, a heater control apparatus 1 includes an oxygen sensor 2. The oxygen sensor 2 is a solid electrolyte type, to which the principles of oxygen ionization are applied. The oxygen sensor 2 includes a pair of electrodes, in each of which a thin layer of platinum is deposited over the surface of a flat film zirconium element. Each electrode has a laminate form in which a platinum electrode, a zirconium element, a platinum electrode, and a zirconium element are placed one over the other in the described order. The zirconium element has a characteristic that the internal resistance (i.e., conductivity) varies in the presence of a difference in oxygen concentration between the two surfaces.

Alternatively, the principles of a high/low concentration battery may be applied to a structure in which a thin layer of platinum electrode is deposited over both inside and outside surfaces of a zirconium element in the form of a test tube.

Furthermore, the internal resistance (i.e., conductivity and electromotive force) has a characteristic that it varies sharply when a theoretical air/fuel ratio is exceeded, such as by a catalyst action of platinum when a temperature of the oxygen sensor 2 has reached a high temperature range exceeding a predetermined temperature. Consequently, the oxygen sensor 2 is mounted on an exhaust pipe. One side of the oxygen sensor 2 is exposed to exhaust gas, while oxygen is introduced into the other side of the oxygen sensor 2, so that a drastic change in internal resistance (i.e., conductivity and electromotive force) will occur near the theoretical air/fuel ratio due to the difference in oxygen concentration between the exhaust gas on one side and the oxygen on the other side.

Still further, the characteristic in which the internal resistance (conductivity and electromotive force) varies drastically coincides with the range of air/fuel ratio where three components of a three-element catalyst would be efficiently purified. Consequently, if a variation of the internal resistance (i.e., conductivity and electromotive force) is detected, and if the air/fuel ratio is controlled, three components, namely CO, HC, and Nox, would be simultaneously purified. Based on the data obtained, the oxygen sensor 2 outputs an oxygen sensor signal so to an internal resistance detecting unit 5.

The heater control apparatus 1 also includes a heater 3. Partly because the heater 3 is disposed in tight contact with the oxygen sensor 2, and partly since the oxygen sensor 2 operates stably within a high temperature range exceeding a predetermined temperature, the heater 3 serves to heat the oxygen sensor 2 to an optimum range of temperature as it is intermittently turned on and off. The intermittent actuation of the heater 3 is controlled by a heater activation signal Hd from a control unit 6.

The exhaust pipe 4 is a large-size pipe having curves which guide exhaust gas, which has been combusted in the internal combustion engine, until it is discharged to the rear of the vehicle. The oxygen sensor 2 for detecting the concentration of oxygen remaining in the exhaust gas is mounted on the exhaust pipe 4 with a sensor element section being positioned in the exhaust pipe 4.

The internal resistance detector 5 is in the form of a memory such as ROM. Correlation data between oxygen sensor signal values and internal resistance values are stored in this ROM.

The internal resistance detector 5 converts an oxygen sensor signal value into an internal resistance value, which has previously been stored in ROM, and vice versa, upon receipt of an oxygen sensor signal So from the oxygen sensor 2. Then, the internal resistance detector 5 sends an internal resistance value corresponding to an oxygen sensor signal value to the control unit 6 as an internal resistance signal Ri.

The control unit 6 includes a microprocessor as a base element, various arithmetic devices, a processing device, a memory, etc. In the memory, process tables/diagrams for data conversion from a correlation of an oxygen sensor surface temperature with an exhaust pipe temperature (See FIG. 3(a)), and a correlation of an internal temperature of resistance with an oxygen sensor surface temperature (See FIG. 3(b)) are stored. Based on this data, the control unit 6 executes data conversion between the oxygen sensor surface temperature and the exhaust pipe temperature, and between the internal resistance and the oxygen sensor surface temperature and controls the timing of turning on and off the electricity to the heater 3 based on the converted data.

Figure 3A:
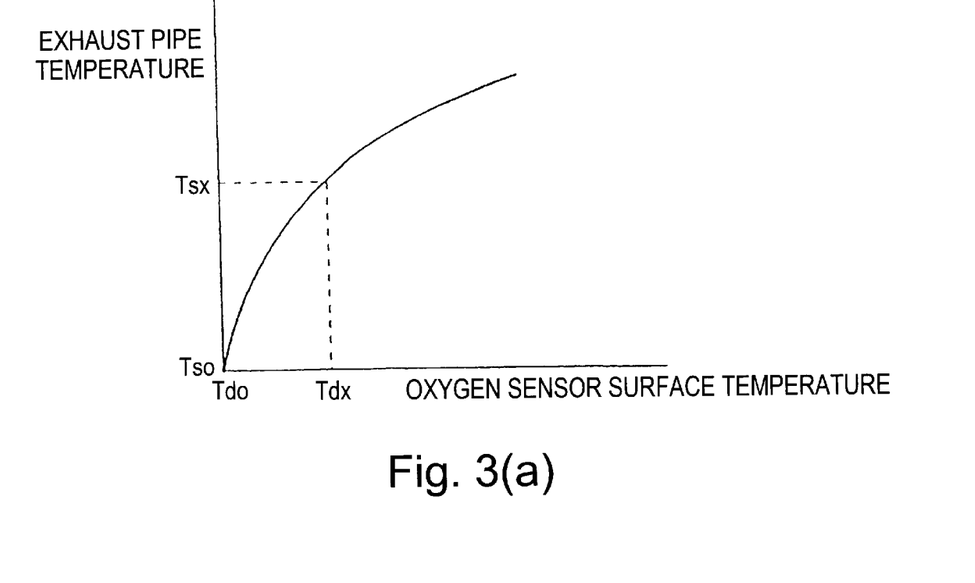
FIG. 3(a) is a diagram showing correlation between an exhaust pipe temperature and an oxygen sensor surface temperature according to the present invention.

As is apparent from the problems to be solved by the present invention, the process table of FIG. 3(a) is used particularly during a period from a point in time immediately after the start of the engine until the exhaust pipe temperature has risen to a sufficiently high temperature.

Upon receipt of an internal resistance signal Ri inputted from the internal resistance detector 5, the control unit 6 calculates an oxygen sensor surface temperature corresponding to an internal resistance signal value from the correlation of the internal resistance with the oxygen sensor surface temperature, then also calculates an exhaust pipe temperature corresponding to the oxygen sensor surface temperature from the correlation of the oxygen sensor surface temperature with the exhaust pipe temperature, and discriminates whether or not the calculated exhaust pipe temperature is less than a predetermined temperature Tsx. If a detected temperature is less than the predetermined temperature Tsx than condensation remains in the exhaust pipe. If the exhaust pipe temperature is within the predetermined range, temperature (i.e., a range of Tsx–Tso), water remains in the exhaust pipe and the control unit 6 initiates control to turn off the electricity to the heater 3. If the exhaust pipe temperature exceeds the temperature Tsx, the control unit 6 initiates control to turn on the electricity to the heater 3.

Still further, upon receipt of an internal resistance signal Ri inputted from the internal resistance detector 5 when the exhaust pipe temperature has exceeded a predetermined temperature (i.e., Tsx), the control unit 6 calculates an oxygen sensor surface, temperature from a correlation of the internal resistance with the oxygen sensor surface temperature, appearing in the process table, and turns on the electricity to the heater 3 by a heater activation signal Hd in such a manner that the oxygen sensor surface temperature is an optimum temperature. This causes the oxygen sensor 2 to operate stably in a high temperature range exceeding a predetermined temperature.

Figure 5A:
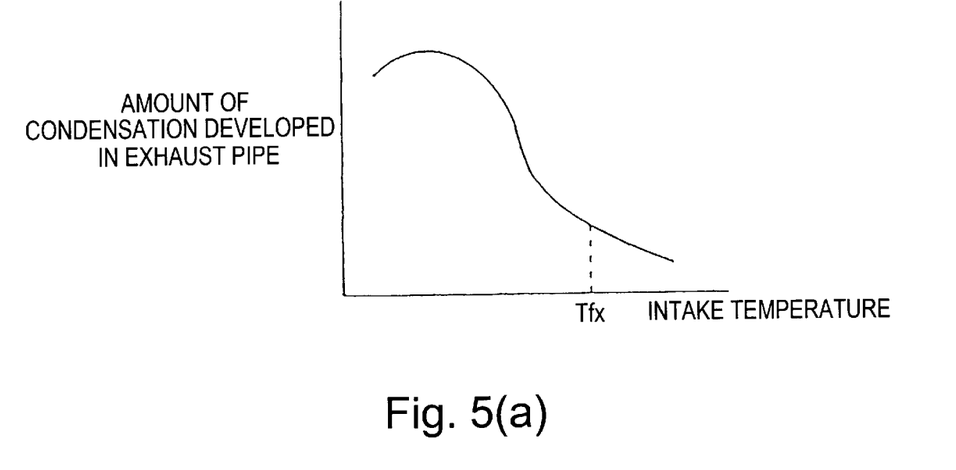
FIG. 5(a) is a diagram showing a correlation between a condensation developing in the exhaust pipe and an intake temperature according to the present invention.

Furthermore, upon receipt of an intake temperature signal Bt inputted from an intake temperature sensor 7, the control unit 6 compares the intake temperature signal Bt with an intake temperature value Tfx, at which less condensation remains, obtained from the correlation of the intake temperature with the amount of condensation developed in the exhaust pipe shown in FIG. 5(a). If the intake temperature signal Bt coincides with Tfx, the control unit 6 judges that a relatively low amount condensation may develop, thus hastening supplying electricity to the heater 3 by the heater activation signal Hd.

Figure 5B:
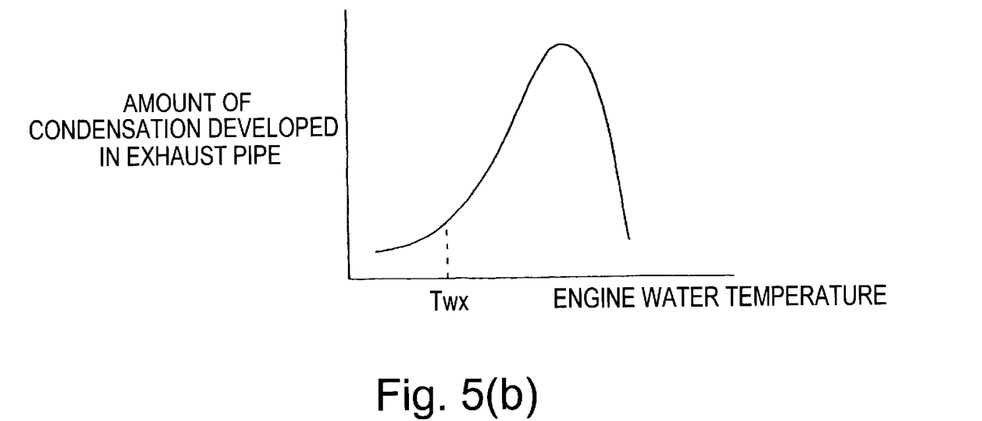
FIG. 5(b) is a diagram showing correlation between a condensation developing in the exhaust pipe and an engine water temperature according to the present invention.

In addition, upon receipt of an engine water temperature signal Ew inputted from an engine water temperature sensor 8, the control unit 6 compares the engine water temperature signal Ew with an engine water temperature value Twx, at which less condensation remains in the exhaust pipe, from the correlation of the engine water temperature with the amount of water drops to develop in the exhaust pipe shown in FIG. 5(b). If the engine water temperature signal Ew is lower than the temperature value Twx, the control unit 6 judges that a relatively low amount condensation may develop in the exhaust pipe, thus hastening supplying electricity to the heater 3 by a heater activation signal.

The foregoing situations of FIGS. 5(a) and 5(b) will now be described in more detail.

When an intake temperature is very low on a severely cold winter morning, for example, condensation tends to develop in the exhaust pipe. On the other hand, when an intake temperature is high during a summer day, for example, condensation is unlikely to develop. Accordingly, if the intake temperature exceeds a predetermined value, it is possible to speed up the starting of turning on the electricity to the heater.

The engine water temperature is high during normal operation of the engine and then drops gradually over a long period of time after the engine stops, whereupon it will be substantially equal to atmospheric temperature after a lapse of an adequate period of time.

When the engine is restarted immediately after being stopped, the water temperature remains almost as it was before the engine was stopped, and so does the exhaust pipe temperature. Under this situation, condensation is unlikely to develop in the exhaust pipe.

Similarly, when the engine water temperature falls sufficiently with a lapse of an adequately long period of time after the engine has stopped, condensation will be unlikely to develop in the exhaust pipe.

On the other hand, when the engine water temperature has insufficiently dropped in temperature with the lapse of a certain period of time after the engine has stopped, only the exhaust pipe temperature falls down to a temperature substantially equal to atmosphere so that condensation will tend to develop in the exhaust pipe.

Namely, since the tendency for development of condensation depends on the level of the engine water temperature even when the exhaust pipe temperature remains at a low level, it is possible to speed up the timing of turning on the electricity to the heater when the engine water temperature is lower than a predetermined level.

The intake temperature sensor 7 is in the form of a temperature detecting element, such as a thermistor, whose sensor section is disposed in an airflow meter, an intake manifold, etc. to detect a temperature of intake air.

The engine water temperature sensor 8 is in the form of a temperature detecting element, such as a thermistor, for detecting an engine coolant water temperature.

The intake temperature sensor 7 outputs an engine water temperature signal Ew, which represents the detected engine coolant water temperature, to the control unit 6.

Thus, with the heater control apparatus of the present invention, because the internal resistance detector for detecting an internal resistance value of the oxygen sensor and the control unit for estimating an oxygen sensor surface temperature based on the internal resistance value detected by the internal resistance detector are provided, then estimating an exhaust pipe temperature based on the estimated oxygen sensor surface temperature and starting to turn on the electricity to the heater, which is combined with the oxygen sensor, when the estimated exhaust pipe temperature has reached a predetermined temperature, it is possible to turn off the electricity to the heater when condensation remains in the exhaust pipe and when the exhaust pipe temperature is low; and to turn on the electricity to the heater until condensation has disappeared in the exhaust pipe because the exhaust pipe temperature has risen, thus controlling the timing of turning on the electricity to the heater with a simple structure.

Figure 2:
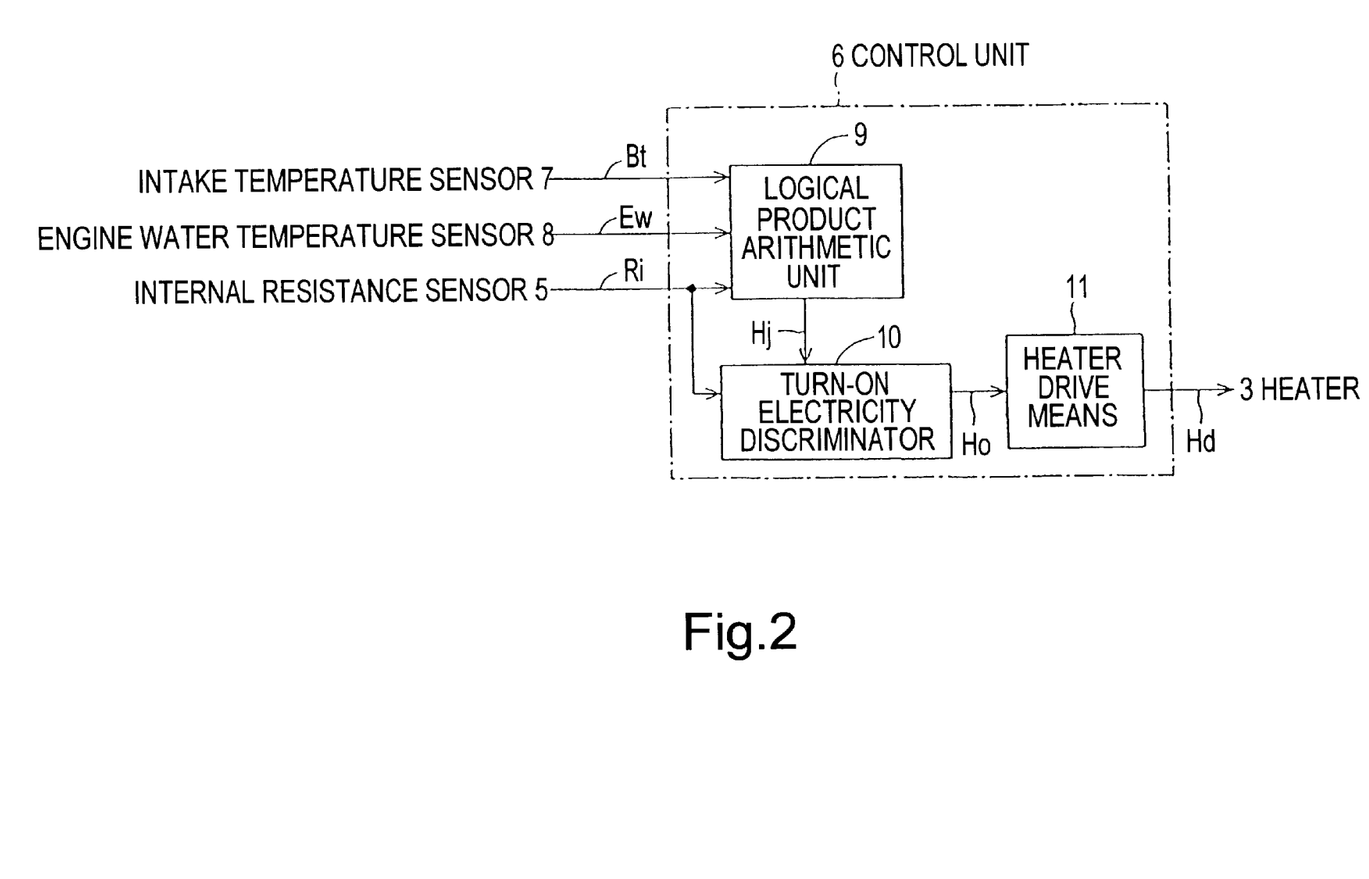
FIG. 2 is a block diagram showing a principal part of a control unit according to the present invention.

As illustrated in FIG. 2, the control unit 6 includes a logical product arithmetic unit 9. The logical product arithmetic unit 9 is composed of an input comparison circuit, such as a comparator, and a logical product arithmetic circuit, such as an AND or NAND gate, for converting the intake temperature signal Bt from the intake temperature sensor 7 and the engine water temperature signal Ew from the engine water temperature detector 8 into digital signals. Then, the unit discriminates from these signals whether or not condensation remains in the exhaust pipe, and performs a logical product operation of these signals with the internal resistance signal Ri.

Furthermore, when the intake temperature signal Bt from the intake temperature sensor 7 and the engine water temperature signal Ew from the engine water temperature detector 8 have not been detected, the logical product arithmetic unit 9 outputs the internal resistance signal Ri from the internal resistance detector 5 to a turn-on-electricity discrimination unit 10 as an operational signal Hj.

The logical product arithmetic unit 9 receives two signals, i.e., the intake temperature signal Bt from the intake temperature sensor 7 and the internal resistance signal Ri from the internal resistance detector 5, converts the intake temperature signal Bt into a digital signal, then inputs both the digital signal and the internal resistance signal Ri to an input comparison circuit, which discriminates whether or not condensation remains in the exhaust pipe, then sends the respective output signals of the input comparison circuit to the 2-input logical product arithmetic circuit, and sends the output of the logical product arithmetic circuit to the turn-on-electricity discrimination unit 10 as an operational signal Hj.

Furthermore, the logical product arithmetic unit 9 receives two signals, i.e., the engine water temperature signal Ew from the engine water temperature detector 8 and the internal resistance signal Ri from the internal resistance detector 5, converts the engine water temperature signal Ew into a digital signal, then inputs both the digital signal and the internal resistance signal Ri to the input comparison circuit, which discriminates whether or not condensation remains in the exhaust pipe, sends the respective outputs of the input comparison circuit to the 2-input logical product arithmetic circuit, and then sends the output of the logical product arithmetic circuit to the turn-on-electricity discrimination unit 10 as an operational signal Hj.

In addition, the logical product arithmetic unit 9 receives three signals, i.e., the intake temperature signal Bt from the intake temperature sensor 7, the engine water temperature signal Ew from the engine water temperature detector 8 and the internal resistance signal Ri from the internal resistance detector 5, converts both the intake temperature signal Bt from the intake temperature sensor 7 and the engine water temperature signal Ew from the engine water temperature detector 8 into digital signals, then inputs both the digital signals and the internal resistance signal Ri to the input comparison circuit, which discriminates whether or not condensation remains in the exhaust pipe, sends the respective output signals of the input comparison circuit to the 3-input logical product arithmetic circuit, and then sends the output of the logical product arithmetic circuit to the turn-on-electricity discrimination unit 10 as an operational signal Hj.

The turn-on-electricity discrimination unit 10 is composed of a comparing and discriminating circuit, such as a comparator, and a logical arithmetic circuit. The turn-on-electricity discrimination unit 10 controls a heater activation unit for starting to turn on the electricity to the heater by an operational signal Hj sent from the logical product arithmetic unit 9, receives the internal resistance signal Ri from the internal resistance detector 5 to the comparing and discriminating circuit in order for the oxygen sensor 2 to operate stably in a high temperature range exceeding a constant level, and then inputs both the output of the comparing and discriminating circuit and the operational signal Hj to the logical arithmetic circuit, thereby controlling the heater activation unit in such a manner that the oxygen sensor 2 will be in a high temperature range exceeding a predetermined constant level.

Furthermore, the turn-on-electricity discrimination unit 10 outputs a heater activation signal Ho to a heater activation unit 11.

The heater activation unit 11 is composed of a power source, a signal amplifier, an output buffer, etc. and energizes the heater 3 by a heater activation signal Hd supplied from the turn-on-electricity discrimination unit 10.

Figure 3B:
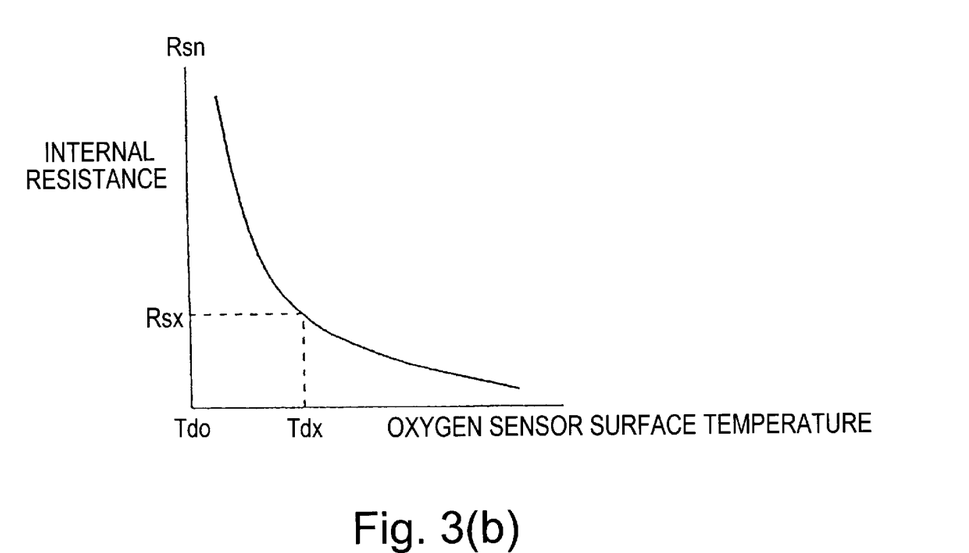
FIG. 3(b) is a diagram showing correlation between an internal resistance and an oxygen sensor surface temperature according to the present invention.

Referring to FIGS. 3(a) and 3(b), both correlation diagrams illustrate a situation where the electricity has not been turned on to the heater immediately after the start of the engine.

It is noted, from the correlation between the exhaust pipe temperature and the oxygen sensor surface temperature of FIG. 3(a) that condensation will develop in the exhaust pipe when the exhaust pipe temperature is in the range of Tso–Tsx.

It is also noted, from the correlation between the internal resistance and the oxygen sensor surface temperature of FIG. 3(b), that condensation will develop in the exhaust pipe when the internal resistance is in the range of Rsn–Rsx while the oxygen sensor surface temperature is in the range of Tdo–Tdx.

Accordingly, by starting to turn on the electricity to the heater when the internal resistance is lower than Rsx, it is possible to control activation of the heater 3 in such a manner that the element temperature of the oxygen sensor 2 will be optimum, which secures a stable operation of the oxygen sensor 2.

Figure 4:
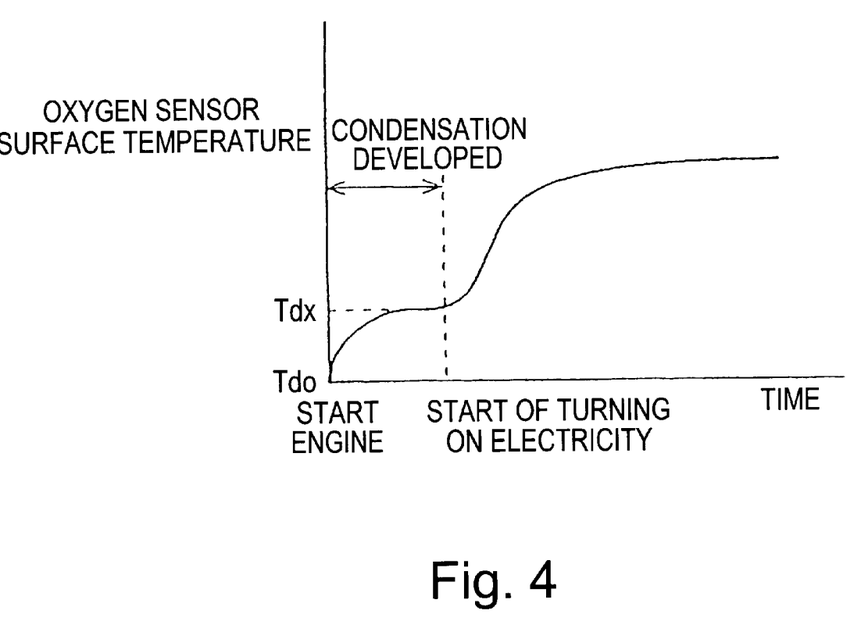
FIG. 4 is a diagram showing a correlation between the oxygen sensor surface temperature and a lapse of time after stating an engine according to the present invention.

FIG. 4 is a diagram showing a correlation between the oxygen sensor 2 surface temperature and a lapse of time. As seen in the figure, since condensation develops when the oxygen sensor surface temperature is in the range of Tdo–Tdx, the electricity to the heater should be supplied at a point in time where the oxygen sensor surface temperature exceeds Tdx; this prevents thermal shock from taking place.

After starting to turn on the electricity to the heater 3, the control unit 6 also detects an internal resistance and repeats turning the electricity to the heater on and off in such a manner that the surface temperature of the oxygen sensor 2 converges at a high temperature range where the oxygen sensor 2 can operate stably.

As seen in FIGS. 5(a) and 5(b), it is apparent from the correlation between the intake temperature and the condensation developing in the exhaust pipe, since significant condensation will develop in the exhaust pipe at the start of the engine when the intake temperature is lower than Tfx, it is possible to speed up the starting of turning on the electricity to the heater 3 immediately when the intake temperature exceeds Tfx.

Furthermore, as is apparent from the correlation between the engine water temperature and the condensation developed the exhaust pipe as shown in FIG. 5(b), since significant condensation would develop in the exhaust pipe when the engine water temperature exceeds Twx, it is possible to accelerate starting of turning on the electricity to the heater compared to where it exceeds Twx, if the engine water temperature is lower than Twx.

In addition, as is apparent from either FIG. 5(a) or FIG. 5(b), when the intake temperature exceeds Tfx and also when the engine water temperature is lower than Twx, it is possible to accelerate starting of turning on the electricity to the heater to the utmost when both of these conditions are fulfilled, if the engine water temperature is lower than Twx, thus enabling a heater control with increased accuracy when the exhaust pipe is free of condensation.

As is mentioned above, according to the heater control apparatus of the present invention, there are provided internal resistance detecting means for detecting an internal resistance value of the oxygen sensor and controlling means for estimating a surface temperature of the oxygen sensor based on the internal resistance value, estimating an exhaust pipe temperature based on the estimated surface temperature of the oxygen sensor and starting to turn on the electricity to a heater, which is combined with the oxygen sensor into a single unit, when the estimated exhaust pipe temperature has reached a predetermined temperature. It is therefore possible to provide an easy-to-assemble, inexpensive heater control apparatus which does not turn on power to a heater while condensation remains in the exhaust pipe because the exhaust pipe temperature is low, and can start turning on the electricity to a heater after a temperature of the exhaust pipe is sufficiently so that condensation disappears, and can control the timing of turning on the electricity to the heater with a simple structure.

According to the preferred arrangement of this invention, partly since the intake temperature sensor for detecting an intake temperature is provided, and partly since the controlling means controls the starting of turning on the electricity to the heater based on the estimated exhaust pipe temperature and the detected intake temperature, it is possible to provide a heat control apparatus which can heat the oxygen sensor while no condensation remains in the exhaust pipe, can prevent thermal shock, and can secure an improved durability, all with a lower cost than the conventional case.

According to another preferred arrangement of this invention, partly since there is provided the engine water temperature sensor is provided for detecting an engine water temperature, and partly since the controlling means controls turning on the electricity to the heater based on the estimated exhaust pipe temperature and the detected engine water temperature, it is possible to provide a heater control apparatus which can heat the oxygen sensor while no condensation remains in the exhaust pipe, can prevent thermal shock and can secure an improved durability, all at a lower cost than in the conventional case.

According to still another preferred arrangement of this invention, partly since the intake temperature sensor and the engine water temperature sensor are provided, and partly since the controlling means controls the timing of turning on the electricity to the heater based on the estimated exhaust pipe temperature, the detected intake temperature and the detected engine water temperature, it is possible to provide a heater control apparatus which can heat the oxygen sensor while no condensation remains in the exhaust pipe, can prevent thermal shock, and can secure an improved durability, all at a lower cost than in the conventional case.

Accordingly it is possible to provide a heater control apparatus which is simple in structure, requires only a short time for maintenance and is hence economical, and is high in reliability, all at a lower cost than conventional devices.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. An apparatus for controlling the timing of initiating a heater by controlling a temperature of an oxygen sensor, which is mountable on an exhaust pipe to control an air/fuel ratio of an internal combustion engine, comprising:

internal resistance detecting means for detecting an internal resistance value of the oxygen sensor; and controlling means for estimating a surface temperature of the oxygen sensor based on the internal resistance value detected by said internal resistance detecting means, then estimating a temperature of the exhaust pipe based on the estimated surface temperature of the oxygen sensor and controlling an initiation of electricity to a heater, which is combined with the oxygen sensor in a single unit, when the estimated temperature of the exhaust pipe has reached a predetermined temperature.

2. The controlling apparatus according to claim 1, further comprising an intake temperature sensor being in communicaiton with said controlling means for detecting an intake temperature, wherein said controlling means controls said initiation of electricity to the said heater based on the estimated temperature of the exhaust pipe and the detected intake temperature.

3. The controlling apparatus according to claim 1, further comprising an engine water temperature sensor being in communication with said controlling means for detecting an engine water temperature, wherein said controlling means controls said initiation of electricity to the heater based on the estimated temperature of the exhaust pipe and the detected engine water temperature.

4. The controlling apparatus according to claim 1, further comprsing an intake temperature sensor and an engine water temperature sensor being both in communication with said controlling means, wherein said controlling means detects an intake temperature and an engine water temperature received from said intake temperature sensor and said engine water temperature sensor respectively, and controls initiation of electricity to said heater based on the estimated temperature of the exhaust pipe, the detected intake temperature and the detected engine water temperature.

5. The controlling apparatus according to claim 1, wherein said controlling means includes a logical product arithmetic means for receiving at least three separate signals thereto.

6. The controlling apparatus according to claim 1, wherein said controlling means includes a logical product arithmetic means for receiving an intake temperature signal, an engine water temperature signal and an internal resistance signal.

7. The controlling apparatus according to claim 1, wherein said controlling means communicates with an electricity initiator circuit thereof for controlling operation of said heater.

8. A heater control apparatus, comprising:

an oxygen sensor for detecting an exhaust gas and an oxygen concentration level;

a heater being in contact with said oxygen sensor, said heater for supplying heat to said oxygen sensor; and controlling means for controlling operation of said heater based on data including at least an oxygen surface temperature and an exhaust pipe temperature.

9. The heater control apparatus according to claim 8, further comprising an internal resistance detector means being in comminication with said oxygen sensor and said controlling means, said internal resistance detector means for providing a converted oxygen sensor signal in the form of an internal resistance value to said controlling means.

10. The heater control apparatus according to claim 9, wherein said controlling means estimates a surface temperature of the oxygen sensor based on the internal resistance value detected by said internal resistance detecting means, then estimating a temperature based on the estimated surface temperature of the oxygen sensor and controlling a initiation of electricity to said heater when the estimated temperature has reached a predetermined temperature.

11. The controlling apparatus according to claim 8, wherein said controlling means includes a logical product arithmetic means for receiving at least three separate signals thereto.

12. The controlling apparatus according to claim 8, wherein said controlling means communicates with an electricity initiator circuit thereof for controlling operation of said heater.

* * * * *